United States Patent [19]

Yannopoulos

[11] Patent Number: 4,614,669

[45] Date of Patent: Sep. 30, 1986

[54] ANTIMONY-DOPED STANNIC OXIDE THICK FILM GAS SENSOR

[75] Inventor: Lymperios N. Yannopoulos, Churchill, Pa.

[73] Assignee: Westinghouse Electric Corp., Pittsburgh, Pa.

[21] Appl. No.: 777,123

[22] Filed: Sep. 18, 1985

Related U.S. Application Data

[62] Division of Ser. No. 567,453, Dec. 30, 1983.

[51] Int. Cl.$^4$ .............................................. B05D 5/12
[52] U.S. Cl. .................................... 427/87; 427/125; 427/126.1; 427/126.3; 427/126.6; 427/372.2
[58] Field of Search .................. 427/125, 126.3, 126.6, 427/126.1, 372.2, 87

[56] References Cited

U.S. PATENT DOCUMENTS

| | | |
|---|---|---|
| 3,644,795 | 2/1972 | Taguchi ................................. 338/34 |
| 3,695,848 | 10/1972 | Taguchi ............................. 73/27 R |
| 3,835,529 | 9/1974 | Taguchi ................................. 29/570 |
| 3,864,628 | 2/1975 | Klass ........................................ 73/23 |
| 3,900,815 | 8/1975 | Taguchi ................................. 338/34 |
| 3,901,067 | 8/1975 | Boardman ............................... 73/23 |
| 4,033,169 | 7/1977 | Fujishiro ................................. 73/23 |
| 4,396,899 | 8/1983 | Ohno ...................................... 338/34 |
| 4,397,888 | 8/1983 | Yannopoulos ................... 427/126.3 |

Primary Examiner—Richard Bueker
Attorney, Agent, or Firm—Thomas R. Trempus

[57] ABSTRACT

A method of preparing an antimony-doped stannic oxide gas detecting film device responsive to the combustible constituents in an environment of interest is disclosed. Stannic oxide is structurally doped with antimony for use as a thick film gas detecting element.

22 Claims, 6 Drawing Figures (LINEAR FORM OF FIG. 4)

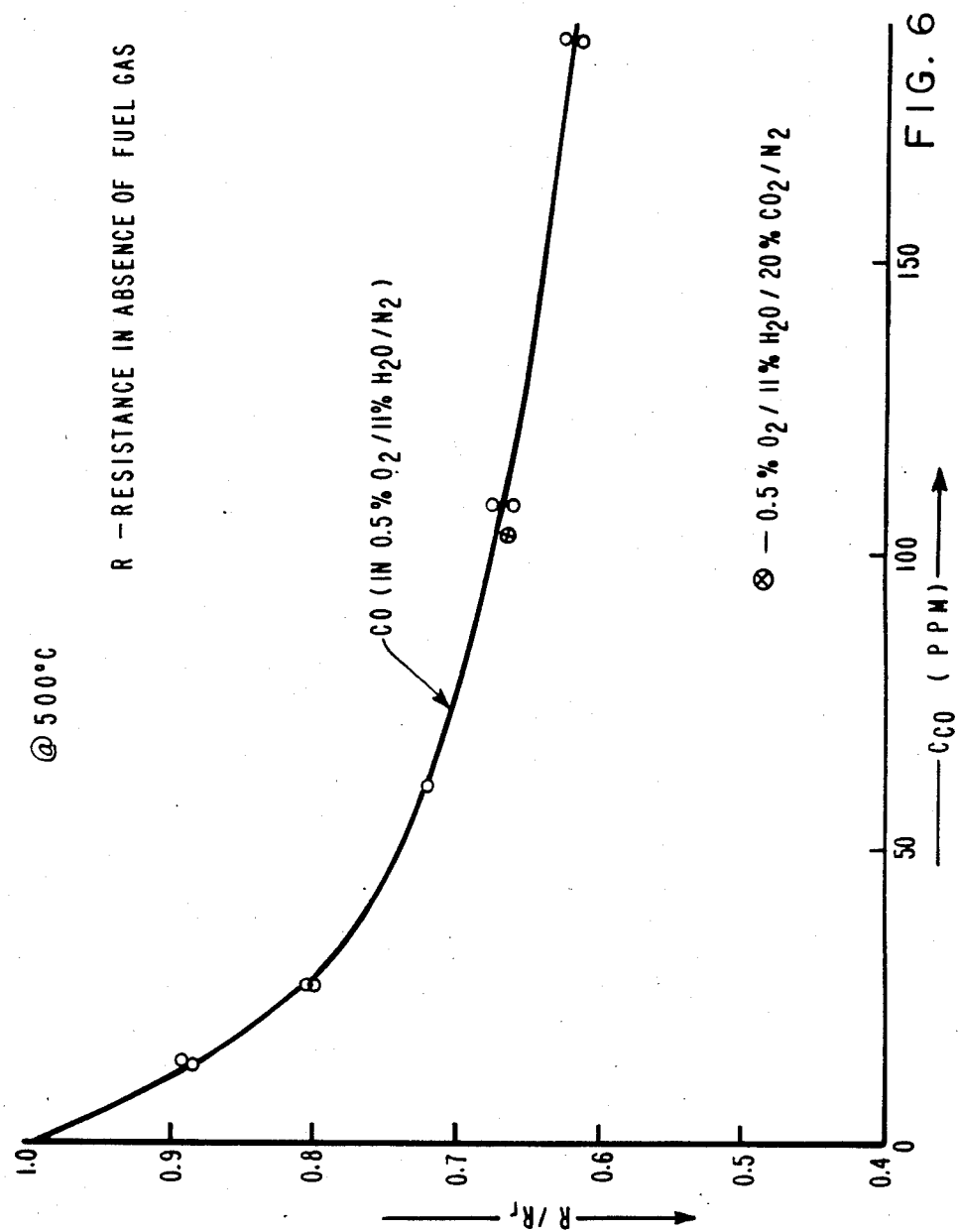

ANTIMONY-DOPED STANNIC OXIDE THICK FILM GAS SENSOR

This is a division of application Ser. No. 06/567,453, filed Dec. 30, 1983.

FIELD OF THE INVENTION

The invention relates to sensors for the monitoring of the concentrations of residual combustible gases; specifically, the invention provides an antimony-doped stannic oxide gas sensor for the detection of hydrogen and carbon monoxide constituents.

BACKGROUND OF THE INVENTION

N-type or p-type semiconductor metal oxides have been considered for the fabrication of gas detecting elements. These are thick films of the semiconductor oxide that have been observed to undergo electrical resistance changes on exposure to combustible gases such as CO and $H_2$. These changes in resistance (R) are related to the concentration (C) of the combustible gas in oxygen-containing atmospheres. An experimentally established R versus C relationship, under conditions that simulate the environment of the application, is used to obtain the concentration of the combustibles.

Stannic oxide ($SnO_2$) has been found to be the most useful n-type semiconductor oxide for the fabrication of thick film combustible gas detecting elements. The response of these elements to reducible type of gases becomes measurable and useful only between 200° and 300° C. and when the conducting oxide is intimately mixed with small amounts of a noble metal catalyst. The gas sensitivity and reproducibility of the detecting elements also require good film mechanical stability and optimum porosity. The electrical resistance in the reference measurement gas should be within a convenient range in order to minimize or eliminate electronic noise problems.

In the current low temperature (200°-300° C.) operated toxic gas detecting elements, the above requirements are achieved by repeated grinding and heating of the starting powder materials. In addition to the semiconductor oxide ($SnO_2$) and the noble metal catalyst, these materials normally include additions of $SiO_2$, $Al_2O_3$ and MgO.

U.S. Pat. No. 4,397,888 assigned to the present assignee and incorporated herein by reference, describes an improved stannic oxide thick film sensor for $H_2$ and CO. That patent teaches the inclusion of specific catalysts and other additives in $SnO_2$ and a unique method for the preparation of the stannic oxide gas detecting film.

It has been the practice to employ stannic oxide-based thick film sensors as detectors of toxic gases in the ambient air environment. For such pollution oriented applications, a small spiral or film resistance heating element is normally used to heat the film sensor to its operational temperature which is approximately 200° C. or greater.

There is a present need to use thick film gas sensors for the in situ monitoring of the concentrations of residual combustible gases in operating gas boilers in order to effect a proper adjustment of the air-to-fuel gas ratio. Such adjustments are required to achieve a desired control of, and optimal efficiency in, the combustion process. In situ sensor operation presents additional constraints. For example, in an operating gas boiler, the combustible gas, thick film sensor is exposed to $N_2/CO_2/H_2O$ vapor/$O_2$ gas mixtures and temperatures as high as at least 500° C. The concentration of $CO_2$ and $H_2O$ in such vapor combustion products is expected to be about 20 and 11 percent, respectively; the concentration of $O_2$, between 5 to 0.1 percent. The balance will be nitrogen. Therefore, the gas film sensors must be more thermally stable than those currently used as toxic gas detectors. Moreover, the sensors must be reproducible and reversible in such a rigorous environment.

It is therefore an object of this invention to provide a thick film gas sensor suitable for a variety of in situ combustion gas monitoring applications.

It is another object of this invention to provide an antimony-doped stannic oxide sensor which is more electronically active and thermally stable than existing stannic oxide based sensors.

It is a further object of this invention to provide a combustible gas sensor having an extended temperature range of response between about 200° C. and at least about 550° C.

It is still another object of this invention to provide a unique method for the fabrication of thick film gas sensing elements, which method facilitates the convenient synthesizing of antimony-doped stannic oxide material and the manufacture of a gas detecting film.

SUMMARY OF THE INVENTION

The invention is an antimony-doped stannic oxide gas sensor element responsive primarily to a combustible constituent in environments of interest. The method includes the following steps: (1) solution precipitation of tin and antimony mixed hydroxide from an admixture of stannic chloride liquid, antimony pentachloride liquid and an ammonium hydroxide solution; (2) drying and calcining the tin and antimony mixed hydroxide precipitate thus rendering an antimony-doped stannic oxide powder; (3) intimately mixing the powder with a noble metal catalyst compound; (4) heating the admixture to effect a good adherence of the catalyst to the powder; (5) adding a sintering agent to the admixture and heating same; (6) mixing the admixture with an organic volatile liquid as a preparation to form a paste; (7) applying the paste to a non-conductive substrate and (8) drying the paste to form an antimony-doped stannic oxide gas detecting film.

BRIEF DESCRIPTION OF THE DRAWINGS

The above as well as other features and advantages of this invention will become apparent through consideration of the detailed description in connection with the accompanying drawings in which:

FIG. 6 is a graph representing the fractional change of film resistance, $R/R_r$, versus the concentration of CO ($C_{CO}$) in 0.5% $O_2$/11% $H_2O$/$N_2$ at 500° C.

DETAILED DESCRIPTION OF THE INVENTION

Figure 1:
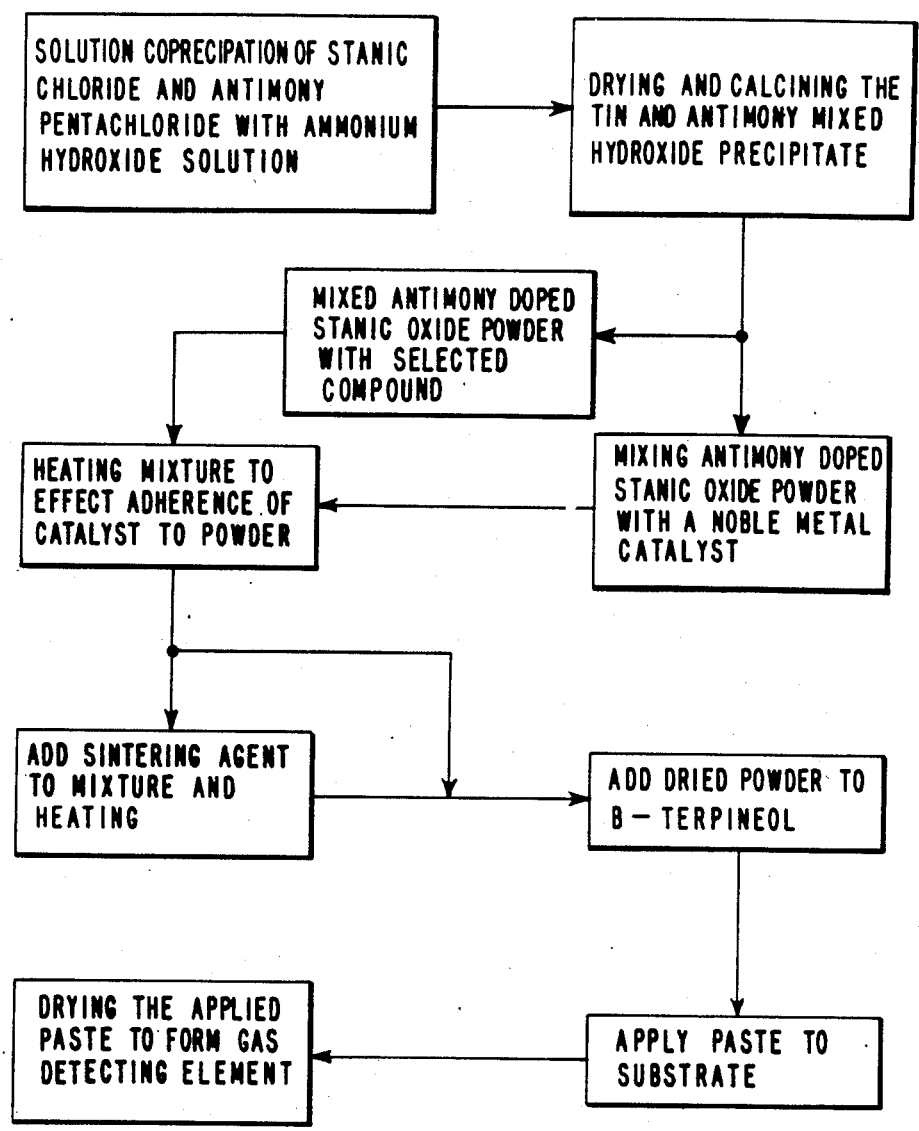
FIG. 1 is a diagram of the process steps for fabricating the improved semiconductor thick film sensor according to this invention.
Figure 3:
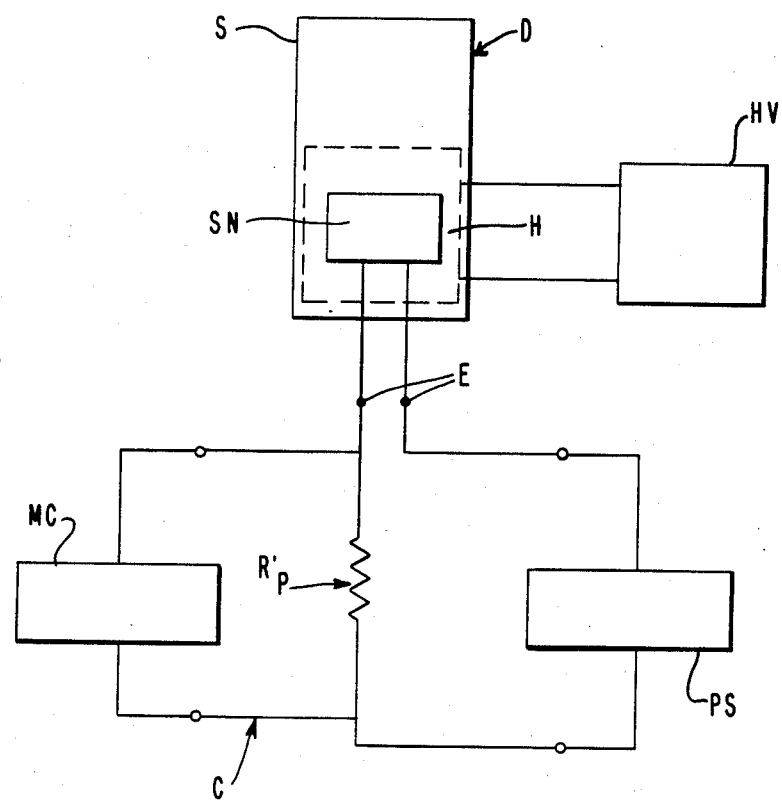
FIG. 3 is a schematic illustration of the application of the thick film sensor material of this invention as a device for the detection of CO and $H_2$ gases.

An improved antimony-doped thick film sensor for hydrogen and carbon monoxide, fabricated in accordance with the process steps detailed in FIG. 1 and typically illustrated in a gas sensing device in FIG. 3, is realized as a result of a preparation procedure whereby an antimony-doped stannic oxide powder is developed through solution processing steps and mixed with a liquid organic volatile to form a paste.

According to this invention, a chemical solution co-precipitation method was used for the preparation of Sb-doped $SnO_2$. The method involves the simultaneous addition of liquids of stannic chloride ($SnCl_4$) and antimony pentachloride ($SbCl_5$) to ammonium hydroxide solution, the formed tin and antimony mixed hydroxide precipitate is dried and then calcined at temperatures between 400° and 800° C. These are much lower temperatures than those required (1400°–1500° C.) for the direct heating of the mixtures of the component oxides.

Figure 2:
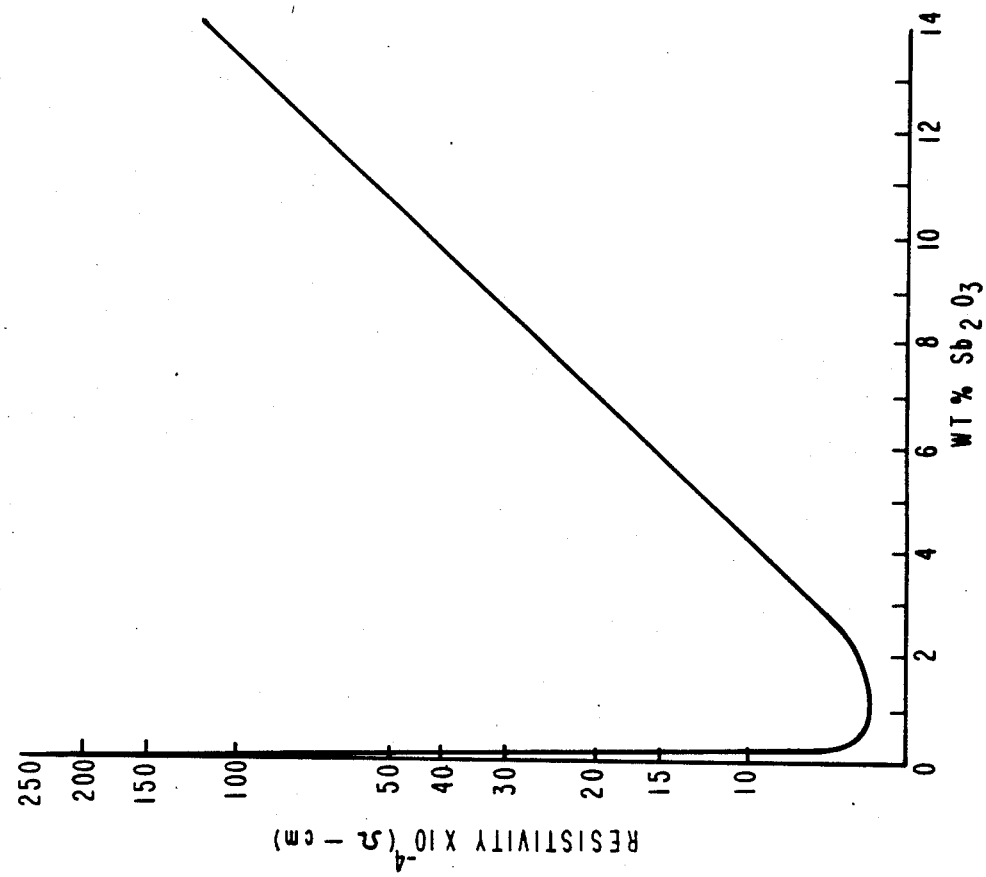
FIG. 2 is a graph representing the resistivity-composition diagram of solid solutions of $Sb_2O_3$ and $SnO_2$.

FIG. 2 illustrates the resistivity-composition diagram of solid solutions of $Sb_2O_3$ and $SnO_2$. The range of minimum resistivity in the graph demonstrates that a range of use of between about 0.5 to 2.5 wt.% $Sb_2O_3$ in the $SnO_2$ renders a more electronically active thick film sensor element with a measurable initial resistance range.

In a typical preparation, a separatory funnel is connected to a three-way flask that contains ammonium hydroxide ($NH_4OH$) solution. The funnel is first purged with nitrogen; nitrogen also flows continuously over the liquid level of $NH_4OH$. The exiting gas is bubbled through water in an Erlenmeyer flask and vented to a hood. Taking precautions to avoid hydrolysis of $SnCl_4$ and $SbCl_5$, the appropriate quantities of the liquid chlorides are added to the oxygen and moisture free separatory funnel which is immediately stoppered. Then, the liquid chloride mixture is added dropwise into the solution of ammonium hydroxide. The amount of reactants used in this preparation were: 600 $cm^3$ of 6N $NH_4OH$ in 1-liter flask, 50 $cm^3$ of $SnCl_4$ and 1 $cm^3$ of $SbCl_5$. This proportion of tin and antimony should produce the equivalent of 1.62 wt.% of $Sb_2O_3$ in solution with $SnO_2$.

The reaction vessel is mounted on an O-ring stand and placed inside a hood. After completion of the reaction is ensured, the contents of the reaction flask are transferred to a 2-liter glass beaker. Some water is added during this step.

The contents of the beaker are centrifuged at 12,000 rpm using stoppered propylene bottles. This step is repeated two more times by adding distilled water after decanting the supernatant liquid each time. After this, the mixed hydroxide slurry is collected in a glass dish and dried on a hot plate (~75° C.) under the hood. The dried mass is then ground in a sapphire mortar and transferred to a quartz boat. The boat is covered with a quartz flat plate and heated to 800° C. inside an air muffle furnace. The furnace has been placed inside a hood. At about 400° C. some smoke was observed. This is apparently the temperature regime of the complete breakdown of the hydroxide structure and the formation of the mixed oxide phase. Within 3 hours of heating, the temperature reached 800° C. and the furnace turned off. p The resulting product oxide is bluish and slightly sintered. The total wt.% loss during the above heating was 15.7%. The product was reground and reheated to 800° C.; it was held at this temperature for 51.5 hours. During this second long heating, the observed weight loss was only 0.1 wt.%. Therefore, the conversion to oxide is essentially complete during the first heating. The bluish color is characteristic of that of the Sb-doped $SnO_2$.

The product powder is very fine ($\leq 43$ $\mu m$); no grinding is required for the preparation of the thick films. This preparation produced 39.1 g of the Sb-doped $SnO_2$ powder. Larger amounts can be easily made. X-ray diffraction analysis showed only the presence of one phase ($SnO_2$).

The as-prepared Sb-doped $SnO_2$ fine powder is intimately mixed with small amounts, 1 to 10%, preferably about 1 to 5%, of a noble metal catalyst compound such as palladium chloride ($PdCl_2$), and heated in an air muffle furnace to 700° C.; a covered aluminum oxide crucible can be used as a container. About one hour of heating at about 700° C. has been found to be adequate; a good adherence of the palladium catalyst to the grains of the Sb-doped $SnO_2$ semiconductor is achieved. At this stage, small amounts of magnesium oxide (MgO) and one or two other selected oxides are added to the above heated powder material. These oxides were: hydrophillic potassium aluminum silicate (molecular sieve powder) and cobalt oxide ($Co_3O_4$). These components are sieved to $\leq 43$ $\mu m$ and intimately mixed with the heat treated mixture of Sb-doped $SnO_2$ and the palladium catalyst. The total mixture is again subjected to the previous heating schedule.

Magnesium oxide and hydrophillic potassium aluminum silicate are particularly effective in enhancing the carbon monoxide sensitivity of the sensor element in the presence of hydrogen. It should be appreciated that hydrophillic additives are useful in environments with low moisture content such as a home furnace or the like, and would therefore not be utilized in a high moisture environment such as a gas boiler as previously discussed.

In a modification of the present invention, the as-prepared Sb-doped $SnO_2$ fine powder is intimately mixed with a small amount of cobalt oxide ($Co_3O_4$) without the aforedescribed use of palladium. The use of cobalt oxide provides an enhanced detection capability for carbon monoxide in the presence of hydrogen and/or hydrocarbons because of its preferential catalytic activity in carbon monoxide combustion. The absence of palladium diminishes the sensor elements response to hydrogen and the presence of cobalt oxide alone renders a sensor element with a promoter catalyst for carbon monoxide selectivity.

These other oxide additives serve as sintering agents (i.e., MgO). Two of these additives, thorium oxide and the molecular sieve powder, are known to have high-temperature hydrophilic sites. In gas sensor applications where the level of the water vapor in the test gas is low and far below the film surface saturation limit, the presence of such hydrophilic sites will preferentially attract the water vapor impurity and will leave the surface of the semiconductor oxide essentially free for oxygen.

It is the catalytically induced interaction of this adsorbed oxygen with the combustible gas that determines the extent of the electron transport process and, thus, the electrical resistance change. In one case, the combined effect of hydrophilic and hydrophobic sites was also examined by the presence of both the hydrophilic potassium aluminum silicate molecular sieve and the hydrophobic silica ($SiO_2$) additives. Cobalt oxide ($Co_3O_4$) was also added to the Sb-doped $SnO_2$ semiconductor without the presence of the palladium catalyst to act as a selective catalyst for CO response, since $Co_3O_4$ is known to be a good combustion catalyst for CO.

The antimony-doped stannic oxide powder composition is prepared as a paste by using a convenient organic volatile liquid as a vehicle for the preparation of the paste. Typically, this can be accomplished by disbursing the sintered stannic oxide powder mixture uniformly in $\beta$-terpineol. The film paste is applied to a nonconductive and inert substrate such as machinable lava of the silicate type across two platinum wire electrodes. The thick film paste is dried to form an antimony-doped stannic oxide gas detecting element. The approximate conductive dimensions of the film were: $0.25 \times 0.07 \times 0.03$ cm. (with 0.07 being the distance between electrodes and 0.03 the thickness).

Turning to FIG. 2, a typical application of a device D utilizing the antimony-doped stannic oxide gas detecting element of the invention is schematically represented. It is to be appreciated that the illustrated embodiment is an exemplar only, and a variety of other substrate geometries and electrode configurations can be employed. The device D includes an inert and non-conductive substrate S onto which a pair of electrodes E are applied. A thick film of antimony-doped stannic oxide sensor paste is applied to the surface of the substrate to effectively bridge the spaced-apart electrodes E. The oxide film sensor SN is in electrical communication with a measuring circuit MC which monitors the output of the sensor SN voltage across the standard resistor $R_p$ of the circuit C. This output is proportional to the resistance R of the device. The resistor $R_p$ is connected in series with a DC power supply PS. The initial output value is predetermined in the absence of a fuel reducing gas mixture. On exposing the sensor SN of the gas measuring device D to a reducing gas mixture, the output changes in voltage as measured by the measuring circuit MC are relative to the concentration of the fuel reducing constituents of the gas mixture. The operating temperature of the device can be achieved through the use of numerous heating techniques, but a preferred technique is a film heater H secured to the substrate S and receiving excitation from a heater voltage source HV. The heater is disposed on the side of the substrate opposite the sensor. In applications where heat is provided by the test chamber, the temperature can be controlled if it is within the sensor response range. Thus, the heater voltage source is not required. An example of such an application in which a heater voltage source is not required is a gas boiler.

The Sb-doped $SnO_2$ thick films of this invention have been found to respond to both $H_2$ and CO present in $O_2/N_2$ and $O_2/N_2/H_2O$ vapor atmospheres. The temperature range of useful response was 200°–550° C. The $H_2$ and CO thick film sensor response to higher temperatures and in the water vapor-containing atmosphere makes the sensors useful for combustion control applications. In gas burning boilers, for example, the combustible gas thick film sensors will be exposed to temperatures as high as 500° C. The desired optimum efficiency and control in gas boilers will be achieved by the proper adjustment of the air-to-fuel ratio. The prop r ratio will be obtained from knowledge of the concentrations of the two main gas boiler residual combustibles ($H_2$, CO) and oxygen. These concentrations will become available by the in situ monitoring with the present Sb-doped $SnO_2$ thick film combustible gas sensor and an oxygen gauge.

The $H_2$ and CO response of our Sb-doped thick films was tested at 500° C. and in a flow (650 cc/min) of $O_2/N_2/H_2O$ vapor mixtures and found to be very good. The changes were proportional to the resistance changes of the films and clearly show the fast and reversible response of the thick film sensor in $O_2/N_2/H_2O$ vapor mixtures of compositions typical of those in gas boilers.

Figure 4:
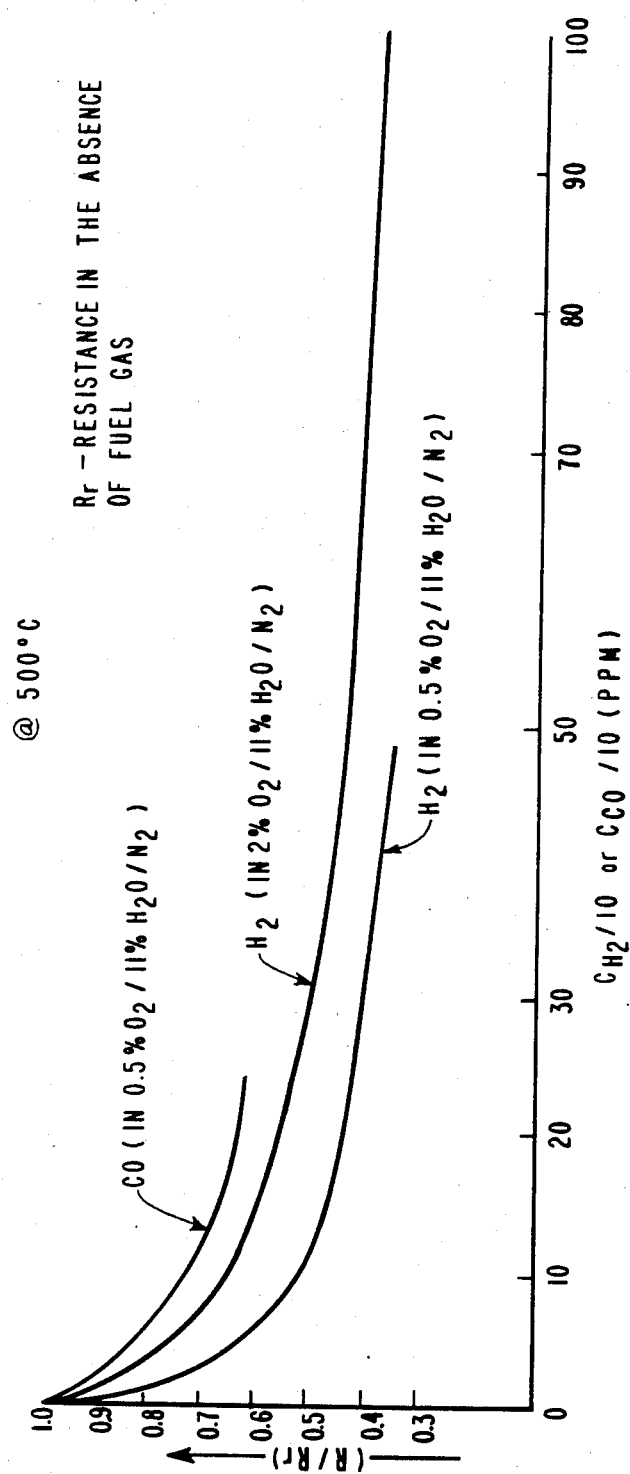
FIG. 4 is a graph representing the fractional change of resistance, $R/R_r$, versus the concentration of CO or $H_2$ at 500° C. (CO in 0.5% $O_2$/11% $H_2O/N_2$; $H_2$ in both 0.5% $O_2$/11% $H_2O/N_2$ and 2% $O_2$/11% $H_2O/N_2$)
Figure 5:
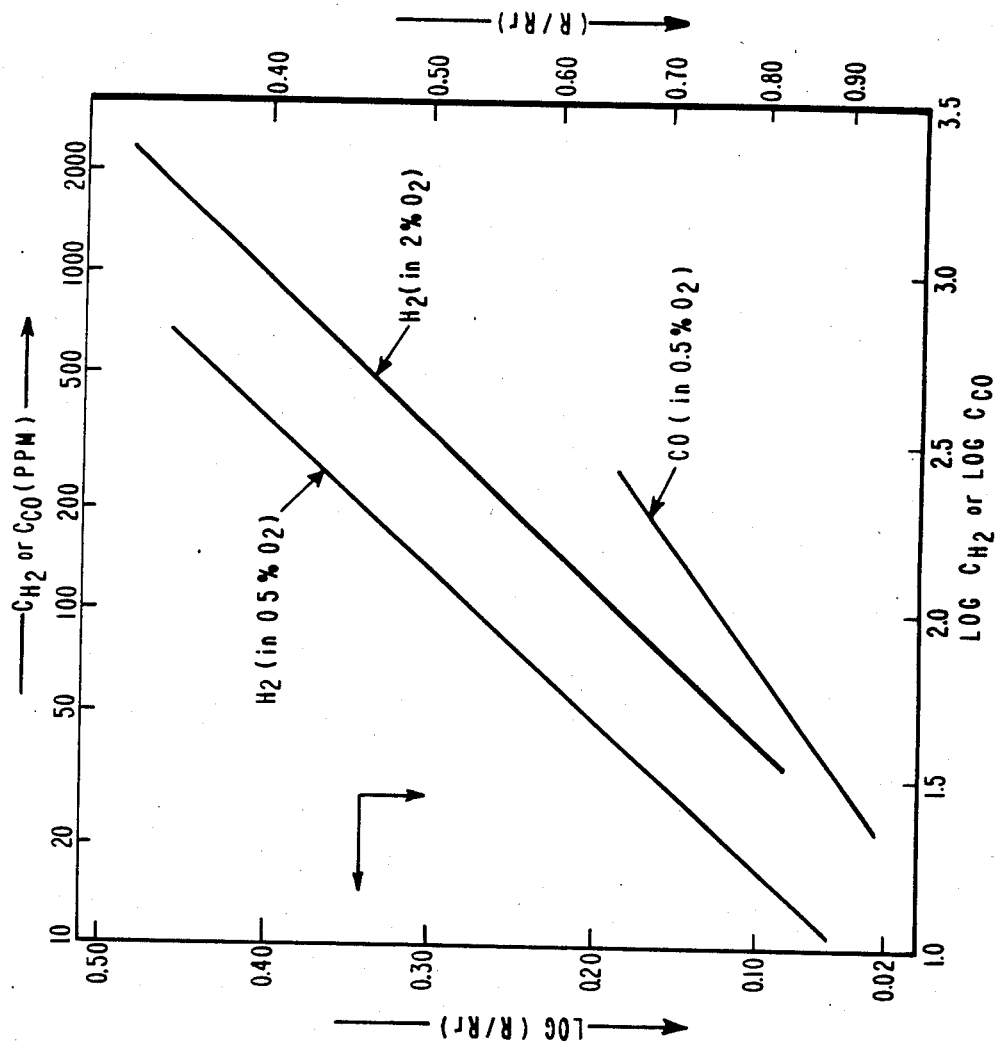
FIG. 5 is a graph representing a log-log plot of the $H_2$ and CO responses of the Sb-doped $SnO_2$ thick film sensor at 500° C. ($H_2$ in 0.5% $O_2$/11% $H_2O/N_2$ and 2% $O_2$/11% $H_2O/N_2$; CO in 0.5% $O_2$/11% $H_2O/N_2$)

The fractional change in the resistance due to the combustible gas is given as $R/R_r$, where $R_r$ is the steady state value resistance of the film with the reference gas and R is that of the combustible gas-doped reference gas. For the tests described above, these $R/R_r$ values are plotted against the concentration, C, of the combustible gas and they are given in FIG. 3. These data can also be linearized on a log-log plot; this is shown in FIG. 4. The effect of $CO_2$, the other major gas component of the combustion products of a gas boiler, was also tested. This is shown in the $R/R_r$ versus C data of FIG. 5. Even at 500° C. the presence of $CO_2$ (x-point on curve), at 20% level in the test gas, did not affect the resistance change due to the combustibles. These data were obtained with a film that had the wt.% composition: Sb-doped $SnO_2$ (97.6), $PdCl_2$ (3.6), MgO (2.9) and $ThO_2$ (5.9). The data of FIG. 6 also show the excellent reproducibility obtained with the Sb-doped $SnO_2$-based thick film sensor.

What has been described is an antimony-doped stannic oxide thick film sensor material and a process for producing the same. A sensor utilizing this thick film material relates observable changes in the electrical resistance of the Sb-doped $SnO_2$-based thick film to the concentration of the combustible gas in oxygen-containing atmospheres.

What is claimed is:

1. A method of preparing an antimony-doped stannic oxide gas detecting film device responsive to combustible constituents in an environment of interest comprising the steps of:
    solution co-precipitation of tin and antimony mixed hydroxide from an admixture of stannic chloride liquid, antimony pentachloride liquid and an ammonium hydroxide solution;
    drying and calcining said tin and antimony mixed hydroxide precipitate, thus rendering an antimony-doped stannic oxide powder;
    intimately mixing said powder with a noble metal catalyst compound;
    heating said intimate admixture to effect a good adherence of said catalyst to said powder;
    adding a sintering agent to said admixture and heating;
    mixing said admixture with an organic volatile liquid as a preparation to form a paste;
    applying said paste to a non-conductive substrate; and
    drying said applied paste to form an antimony-doped stannic oxide gas detecting film.

2. The method of preparing an antimony-doped stannic oxide gas detecting film device according to claim 1 wherein the step of calcining the predried tin and antimony mixed hydroxide precipitate occurs at a temperature between 400° and 800° C.

3. The method of preparing an antimony-doped stannic oxide gas detecting film device according to claim 1 wherein the noble metal catalyst compound is palladium chloride and wherein the step of heating the intimate admixture to effect a good adherence of said catalyst to the powder occurs at about 700° C. for a duration of about one hour.

4. The method of preparing an antimony-doped stannic oxide gas detecting film device according to claim 1 wherein the sintering agent includes magnesium oxide and the admixture includes at least one member selected from the group consisting of potassium aluminum silicate and cobalt oxide.

5. The method of preparing an antimony-doped stannic oxide gas detecting film device according to claim 1 wherein the organic volatile liquid is β-terpineol.

6. The method of preparing an antimony-doped stannic oxide gas detecting film according to claim 2 wherein the step of calcining the predried tin and antimony mixed hydroxide precipitate preferably occurs at a temperature of about 800° C. to form a homogeneous oxide powder.

7. The method of preparing an antimony-doped stannic oxide gas detecting film according to claim 1 wherein the antimony is between about 0.5 and 2.5 wt.% of the antimony-doped stannic oxide constituent.

8. A method of preparing an antimony-doped stannic oxide gas detecting film device responsive to combustible constituents in an environment of interest comprising the steps of:
    solution co-precipitation of tin and antimony mixed hydroxide from an admixture of stannic chloride liquid, antimony pentachloride liquid and an ammonium hydroxide solution;
    drying and calcining said tin and antimony mixed hydroxide precipitate, thus rendering an antimony-doped stannic oxide powder;
    intimately mixing said powder with at least one of the compounds selected from the group consisting of palladium chloride, potassium aluminum silicate and cobalt oxide;
    heating said intimate admixture to effect a good adherence of said compound to said powder;
    adding a sintering agent to said admixture and heating;
    mixing said admixture with an organic volatile liquid as a preparation to form a paste;
    applying said paste to a non-conductive substrate; and
    drying said applied paste to form an antimony-doped stannic oxide gas detecting film.

9. The method of preparing an antimony-doped stannic oxide gas detecting film device according to claim 8 wherein the at least one compound selected is cobalt oxide wherein the cobalt oxide promotes carbon monoxide sensitivity of said device.

10. The method of preparing an antimony-doped stannic oxide gas detecting film device according to claim 8 wherein the at least one compound selected is cobalt oxide and potassium aluminum silicate wherein the resulting device is useful in low moisture content environments.

11. The method of preparing an antimony-doped stannic oxide gas detecting film device according to claim 8 wherein the at least one compound selected is cobalt oxide and palladium chloride wherein the resulting device is particularly useful in the monitoring of carbon monoxide and hydrogen.

12. The method of preparing an antimony-doped stannic oxide gas detecting film device according to claim 11 wherein the selected compounds include potassium aluminum silicate wherein the resulting device is effective in low moisture content environments.

13. The method of preparing an antimony-doped stannic oxide gas detecting film device according to claim 8 wherein the sintering agent is magnesium oxide.

14. The method of preparing an antimony-doped stannic oxide gas detecting film device according to claim 8 wherein the organic volatile liquid is β-terpineol.

15. The method of preparing an antimony-doped stannic oxide gas detecting film according to claim 8 wherein the antimony is between about 0.5 and 2.5 wt.% of the antimony-doped stannic oxide constituent.

16. The method of preparing an antimony-doped stannic oxide gas detecting film device according to claim 8 wherein the intimately mixed compound is potassium aluminum silicate which compound also acts as the added sintering agent.

17. A method of preparing an antimony-doped stannic oxide gas detecting film device responsive to combustible constituents in an environment of interest comprising the steps of:
    solution co-precipitation of tin and antimony mixed hydroxide from an admixture of stannic chloride liquid, antimony pentachloride liquid and an ammonium hydroxide solution;
    drying and calcining said tin and antimony mixed hydroxide precipitate, thus rendering an antimony-doped stannic oxide powder wherein the antimony is between about 0.5 and 2.5 wt.% of the antimony-doped stannic oxide;
    intimately mixing said powder with at least one of the compounds selected from the group consisting of palladium chloride, potassium aluminum silicate and cobalt oxide; p1 heating said intimate admixture to effect a good adherence of said compound to said powder;
    adding magnesium oxide as a sintering agent to said admixture and heating;
    mixing said admixture with β-terpineol, an organic volatile liquid, as a preparation to form a paste;
    applying said paste to a non-conductive substrate; and
    drying said applied paste to form an antimony-doped stannic oxide gas detecting film.

18. The method of preparing an antimony-doped stannic oxide gas detecting film device according to claim 17 wherein the at least one compound selected is cobalt oxide wherein the cobalt oxide promotes carbon monoxide sensitivity of said device.

19. The method of preparing an antimony-doped stannic oxide gas detecting film device according to claim 17 wherein the at least one compound selected is cobalt oxide and potassium aluminum silicate wherein the resulting device is useful in low moisture content environments.

20. The method of preparing an antimony-doped stannic oxide gas detecting film device according to claim 17 wherein the at least one compound selected is cobalt oxide and palladium chloride wherein the resulting device is particularly useful in the monitoring of carbon monoxide and hydrogen.

21. The method of preparing an antimony-doped stannic oxide gas detecting film device according to claim 17 wherein the selected compounds include potassium aluminum silicate wherein the resulting device is effective in low moisture content environments.

22. The method of preparing an antimony-doped stannic oxide gas detecting film device according to claim 17 wherein the intimately mixed compound is potassium aluminum silicate which compound also acts as the added sintering agent.

* * * * *